United States Patent [19]

Chiesi et al.

[11] Patent Number: 5,504,105
[45] Date of Patent: Apr. 2, 1996

[54] PHARMACEUTICAL COMPOSITIONS CONTAINING IPRIFLAVONE, PROCESS FOR THE PREPARATION THEREOF AND RELATIVE THERAPEUTIC USE

[75] Inventors: Paolo Chiesi; Luciana Pavesi, both of Parma, Italy

[73] Assignee: Chinoin Pharmaceutical and Chemical Works Co. Ltd., Budapest, Hungary

[21] Appl. No.: 177,798

[22] Filed: Jan. 6, 1994

Related U.S. Application Data

[63] Continuation of Ser. No. 934,621, Aug. 28, 1992, abandoned.

[30] Foreign Application Priority Data

Mar. 23, 1990 [IT] Italy ......................... 19793/90

[51] Int. Cl.⁶ .................................................. A61K 31/35
[52] U.S. Cl. .................................................. 514/456
[58] Field of Search .................................. 514/456

[56] References Cited

U.S. PATENT DOCUMENTS

| 4,639,466 | 1/1987 | Huang et al. ............. 514/456 |
| 4,999,378 | 3/1991 | Fujii et al. .............. 514/567 |

OTHER PUBLICATIONS

American Pharmaceutical Assoc., *Handbook of Pharmaceutical Excipients*, 1986, pp. 165 and 314.
Agnusdei et al., *Biosis Abstracts*, vol. 88, No. 53420, 1989.
Bossanyi et al., *Medline Abstracts*, No. 89383512, 1989.
Weiszfeiler, et al., *Chemical Abstracts* 112(8):62471u, 1988.

*Primary Examiner*—Marianne M. Cintins
*Assistant Examiner*—William R. A. Jarvis
*Attorney, Agent, or Firm*—Birch, Stewart, Kolasch & Birch

[57] ABSTRACT

Oral pharmaceutical compositions containing Ipriflavone comprising oily vehicles that promote absorption of the drug enabling the dosage to be simplified.

2 Claims, No Drawings

PHARMACEUTICAL COMPOSITIONS CONTAINING IPRIFLAVONE, PROCESS FOR THE PREPARATION THEREOF AND RELATIVE THERAPEUTIC USE

This is a continuation of application Ser. No. 934,621 filed Aug. 28, 1992, now abandoned.

This application is a 371 of PCT/EP/91/00528, filed Mar. 19, 1991.

The present invention relates to ipriflavone oral pharmaceutical compositions and to the process for their preparation.

Ipriflavone is an isoflavone derivative of formula:

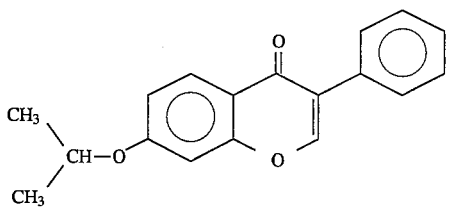

It is effective in preventing and treating post-menopausal and senile osteoporosis.

When administered orally in man, ipriflavone is absorbed rapidly and, furtherly, extensively metabolised equally rapidly: only minimal amounts of unchanged ipriflavone can be found in the blood, where its metabolites predominate. The peak plasma concentration of the unchanged drug (170 ng/ml) is reached 1.3 hours after administration, and the half-life is 9.8 hours.

Seven metabolites of ipriflavone have been identified, five of which inhibit bone resorption. The potency of metabolites 1, 2 and 5 in particular is equal to that of the precursor. It is therefore believed that the action of the antiosteoporotic properties of the drug derive from the cumulative effect of ipriflavone and its metabolites.

The pharmaceutical composition of ipriflavone currently available is in the form of tablets each containing 200 mg of active ingredient. Bioavailability studies conducted with this formulation have shown that the optimum daily dose is 600 mg, which is achieved by administering one tablet three times daily.

Repeated drug assumptions are unpleasant to patients, especially in the case of long-term treatment where concomitant therapy is often necessary.

On the other hand, an active ingredient must be present at its site of action in adequate concentrations in order to exert its pharmacological effects. These concentrations depend on various factors such as the degree and rate of absorption, distribution and localisation in the tissues, metabolisation, and elimination. All these factors are in turn affected by the chemical and physical properties of the drug molecule.

One of the basic aims of modern pharmaceutical technology is to develop appropriate release systems that will take account of all these variables and provide for each drug a dosage regimen that is more practical and acceptable to the patient and will therefore ensure more effective use of the drug in clinical practice.

The present invention relates to new oral pharmaceutical compositions of ipriflavone having the advantage of making the drug available to the body in sufficient quantities to produce the desired pharmacological response and maintain this activity for a sufficient time for the dosage to be simplified to one or two doses daily.

A first aspect of the invention is an oral pharmaceutical composition, characterised in that the active ingredient is dispersed in an adjuvant selected from hydrogenated vegetable oils, monoglycerides, diglycerides, medium-chain triglycerides or their mixtures, white chocolate and soya lecithin, in a quantity of at least 50% by weight per unit dose The mixture thus obtained is enclosed in soft gelatin capsules (Scherer® capsules) or packed in other suitable container.

It is known that oily vehicles could be used advantageously in order to accelerate or increase the absorption of therapeutic agents with unreliable bioavailability characteristics.

However, the basic mechanisms of the interaction between drug and vehicle are still largely unknown and there are no reliable criteria that can be generally applied when developing a new formulation.

The principal parameters that determine the release characteristics of a pharmaceutical composition of this type are the affinity of the active constituent for the vehicle, the quantity and properties of the vehicle and the weight ratio of vehicle to active ingredient. It has now been found that by dispersing ipriflavone in an oily vehicle or adjuvant,containing suitable solubilising and emulsifying agents, the quantity of vehicle to unit dose being as above described, and enclosing this mixture in a pharmaceutical composition for oral administration an improved absorption of the drug is obtained.

A second aspect of the invention therefore relates to a process for the preparation of pharmaceutical compositions of ipriflavone for oral administration in oily vehicles.

The following examples will further illustrate the invention. The quantities of constituents given in the examples are sufficient for the preparation of 10,000 capsules.

EXAMPLE 1

Preparation of the mixture containing the active ingredient (unit dose 300 mg)

700 grams of hydrogenated vegetable oils are melted with heating, at a temperature not exceeding 40° C., in 2.6 kg of medium-chain triglycerides. 500 g of soya locithin are added, the whole is mixed and left to cool to room temperature. 3 kg of ipriflavone are added, and the whole is mixed for approximately 10 minutes. The mixture thus obtained is milled in a three-cylinder refiner, the paste is sieved through a 400μ sieve, and finally de-aeration is carried out.

Unit composition of the mixture containing the active ingredient.

| IPRIFLAVONE | 300.0 mg |
| SOYA LECITHIN | 50.0 mg |
| MEDIUM-CHAIN TRIGLYCERIDES | 260.0 mg |
| HYDROGENATED VEGETABLE OILS | 70.0 mg |
| Total weight of the content | 680.0 mg |

The weight ratio of the constituents of the oily vehicle can be changed without any significant effect on the absorption characteristics of the active ingredient.

EXAMPLE 2

Preparation of the gelatin mass for the formation of the gelatin shell.

Powdered gelatin, glycerol and purified water are mixed in a planetary mixer for approximately 10 minutes, after which the whole is melted in a suitable melting device for approximately 3 hours at about 70° C. under vacuum. After melting, the preservatives and dyes are added, selected from ethyl sodium p-hydroxybenzoate, propyl sodium p-hydroxybenzoate, red ferrous oxide, orange-yellow and titanium dioxide.

EXAMPLE 3

Preparation of the capsules.

The hot gelatin mass obtained as described in example 2 is used to prepare the capsules, which are filled with the mixture containing the active ingredient, using a Scherer automatic machine, by the usual known industrial methods.

Similarly to example 1 the following composition containing 600 mg of ipriflavone per unit dose can be prepared.

EXAMPLE 4

Composition containing 600 mg of ipriflavone per unit dose

| | |
|---|---:|
| Palmitic and stearic acid mono-di-tri-glycerides mixture | 56.000 mg |
| White chocolate | 600.000 mg |
| Medium-chain triglycerides | 871.000 mg |
| Soya lecithin | 27.000 mg |
| Ipriflavone | 600.000 mg |
| Sodium saccharin | 1.000 mg |
| Sorbitol | 300.000 mg |
| Orange flavour | 25.000 mg |
| Total weight of the content | 2480.000 mg |

The composition can be enclosed in a squeezeable soft gelatin capsule or in another suitable device. The container is opened at the time of administration and the content is squeezed onto a spoon or directly into the oral cavity and immediately swallowed. The 600 mg ipriflavone composition is even more advantageous since it enables a once a day dosage schedule.

In-Vivo Bioavailability Tests

The bioavailability of the pharmaceutical composition described in Examples 1–3 was determined in a study conducted in 8 healthy adult volunteers between 21 and 34 years of age, in good physical condition.

The drug was administered as 300 mg capsules throughout the period of treatment (from the 1st to the 9th day inclusive) at the rate of one capsule twice a day (giving a total of 600 mg) taken after food at 8 am and 8 pm.

On the tenth day only the morning dose (8 am) was administered. Concomitant drug treatment was avoided.

Plasma and urine levels of ipriflavone and its metabolites—metabolite 1 (M1), metabolite 2 (M2), metabolite 3 (M3), metabolite 5 (M5)—were then measured.

Blood samples were collected on the first day before starting the treatment, on the seventh day in the morning before meals and before drug administration, and on the tenth day at time 0 (before meals and before the planned single daily dose) and then 0.5, 1, 2, 3, 4, 8, 12, 24, 36, 48 hours after the treatment.

The heparinised blood samples were centrifuged within 15 minutes after collection and the separated plasma stored at −20° C. until analysed by HPLC.

Urine was collected over the 24 hour period before treatment and on the tenth and eleventh days over the periods 0–24 hours and 24–48 hours after the assumption of the last dose. A homogenous sample (10 ml approx.) was prepared from the total urine excreted on the tenth and eleventh days; this sample was then stored at −20° C. until analised by HPLC.

The pharmacokinetic data were compared with those obtained administering an equivalent dose of ipriflavone in the standard formulation of 200 mg tablets three times daily (total dose 600 mg) according to an analogous study protocol.

Table 1 shows the main pharmacokinetic parameters of ipriflavone and its metabolites after administration of 300 mg capsules according to the invention:

area under the plasma concentration-time curve (AUC) on the 10th day at steady state during the 0–48 h period and during the dosage time interval, i.e. AUC (0–8 h) for the tablets and AUC (0–12 h) for the capsules;

maximum plasma concentration (Cmax) calculated directly from the experimental data;

minimum plasma concentration (Cmin) corresponding to time 0 on the 10th day (before the morning dose);

time to reach the peak plasma level (Tmax);

means concentration at steady-state, calculated using the formula:

$$\frac{AUC}{\tau}$$

where $\tau$ is the dosage interval.

Table 2 shows the same data for the reference composition of 200 mg standard tablets.

TABLE 1

Mean pharmacokinetic parameters (n = 8) on ipriflavone and its metabolites M1, M2, M3, M5 after administration of two 300 mg ipriflavone capsules per day (mean values ± S.D.)

| | | AUC(0–48 h) (ng/ml) * h | AUC(0–12 h) (ng/ml) * h | C. MAX ng/ml | C. MIN ng/ml | C ng/ml | T. MAX h |
|---|---|---|---|---|---|---|---|
| IPRIFLAVONE | Mean | 2714.76 | 954.30 | 117.08 | 74.39 | 79.53 | 9.00 |
| | S.D. | 536.07 | 188.01 | 27.25 | 14.16 | 15.67 | 4.73 |
| METABOLITE 1 | Mean | 6038.66 | 2543.32 | 333.34 | 280.70 | 211.94 | 2.00 |
| | S.D. | 1298.70 | 553.36 | 56.74 | 52.01 | 46.11 | 0.50 |
| METABOLITE 2 | Mean | 3082.75 | 1304.87 | 172.35 | 145.76 | 108.74 | 19.19 |
| | S.D. | 1216.03 | 519.72 | 65.71 | 62.19 | 43.33 | 8.45 |

TABLE 1-continued

Mean pharmacokinetic parameters (n = 8) on
ipriflavone and its metabolites M1, M2, M3, M5 after
administration of two 300 mg ipriflavone capsules per
day (mean values ± S.D.)

|  |  | AUC(0–48 h) (ng/ml) * h | AUC(0–12 h) (ng/ml) * h | C. MAX ng/ml | C. MIN ng/ml | C ng/ml | T. MAX h |
|---|---|---|---|---|---|---|---|
| METABOLITE 3 | Mean | 1321.82 | 584.27 | 90.55 | 37.56 | 48.69 | 2.19 |
|  | S.D. | 230.21 | 112.77 | 14.43 | 16.24 | 9.40 | 0.94 |
| METABOLITE 5 | Mean | 9669.64 | 4307.15 | 624.92 | 479.68 | 358.93 | 1.06 |
|  | S.D. | 1116.51 | 519.54 | 80.82 | 89.26 | 43.30 | 0.22 |

TABLE 2

Mean pharmacokinetic parameters (n = 8) of ipriflavone and its metabolites M1, M2,
M3, M5 after administration of three 200 mg ipriflavone capsules per day (mean values ±
S.D.)

|  |  | AUC(0–48 h) (ng/ml) * h | AUC(0–12 h) (ng/ml) * h | C. MAX(a) ng/ml | C. MIN(a) ng/ml | C(a) ng/ml | T. MAX(a) h |
|---|---|---|---|---|---|---|---|
| IPRIFLAVONE | Mean | 2021.57 | 475.42 | 109.90 | 85.13 | 59.43 | 1.25 |
|  | S.D. | 1189.89 | 178.26 | 19.69 | 14.37 | 22.28 | 0.31 |
| METABOLITE 1 | Mean | 9325.69 | 2369.97 | 397.88 | 346.77 | 259.85 | 1.25 |
|  | S.D. | 665.86 | 274.46 | 117.53 | 33.03 | 34.31 | 0.49 |
| METABOLITE 2 | Mean | 511.00 | 267.89 | 82.66 | 58.61 | 33.49 | 12.94 |
|  | S.D. | 203.52 | 85.65 | 26.37 | 28.75 | 10.71 | 7.66 |
| METABOLITE 3 | Mean | 6088.63 | 2058.01 | 369.73* | 225.63* | 250.22* | 2.06 |
|  | S.D. | 1043.12 | 376.64 | 74.78 | 20.54 | 42.34 | 0.63 |
| METABOLITE 5 | Mean | 9021.46 | 3108.05 | 579.56 | 455.73 | 388.51 | 1.56 |
|  | S.D. | 966.39 | 416.19 | 74.55 | 66.58 | 52.02 | 0.58 |

(a) = value compared by the Mann-Whitney U test (p<0.05)
*significant difference To compare the AUC values of the two compositions at steady state on the 10th day, the areas in the respective dosage time intervals were calculated and then the AUC values of the capsules (0–12 h) were multiplied by two and the AUC values of the tablets (0– 8 h) by three. The AUC values of the 24-hour period taking into account the different dosage scheme were so obtained.

The values of ipriflavone, the sum of the main metabolites (M1, M5) and the sum of all the metabolites (M1, M2, M3 and M5) are given in Table 3.

The plasma levels of metabolite 3 were lower with the capsules than with the tablets, but this finding is not particularly significant since this metabolite is the least important in respect of therapeutic activity.

Tables 4 and 5 show the urinary excretion values of metabolites M1, M2 and M5. There were no detectable levels of unchanged ipriflavone.

TABLE 3

Calculation of the AUC values of the total
dose of 600 mg per day of ipriflavone administered over
the 24-hour period (n = 8)

| COMPOSITION |  | IPRIF | M1 + M5 | M1 – M2 – M3 – M5 |
|---|---|---|---|---|
| Capsules | Mean | 1908.61 | 14962.87 | 18761.16 |
| 300 mg × 2 | S.D. | 376.01 | 2263.90 | 2589.26 |
| AUC (0–12 h) × 2 |  |  |  |  |
| Tablets | Mean | 1426.25 | 16434.06 | 23411.76 |
| 200 mg × 3 | S.D. | 534.79 | 1867.72 | 2921.14 |
| AUC (0–8 h) × 3 |  |  |  |  |

As shown in the Tables, there were no significant difference in the pharmacokinetic behaviour of ipriflavone and its metabolites given in the two formulations.

The levels of metabolite 2 were higher with the capsules but this may have been due, according to our observations, to interference with the diet.

Over both time intervals considered, both the quantities excreted and the concentration per ml of urine found for the capsules were much higher than the respective values for the tablets.

Both these increases (total mg and mg per ml) were statistically significant for all the metabolites.

TABLE 4

Urinary levels of metabolite 1, metabolite 2 and metabolite 5 (10th day) after repeated administration of two 300 mg capsules of ipriflavone per day (mean values ± S.D.)

|  |  | (0–24) | | | (24–48) | | |
|---|---|---|---|---|---|---|---|
|  |  | ml | mg | % DOSE | ml | mg | % DOSE |
| METABOLITE 1 | Mean | 1438.63 | 33.37 | 5.55 | 1225.00 | 14.12 | 2.35 |
|  | S.D. | 193.60 | 6.10 | 1.02 | 90.14 | 4.65 | 0.78 |
| METABOLITE 2 | Mean | 1438.63 | 23.22 | 3.87 | 1225.00 | 8.61 | 1.43 |
|  | S.D. | 193.60 | 7.91 | 1.32 | 90.14 | 1.76 | 0.29 |
| METABOLITE 5 | Media | 1438.63 | 109.01 | 18.17 | 1225.00 | 65.68 | 10.95 |
|  | S.D. | 193.60 | 24.77 | 4.13 | 90.14 | 26.74 | 4.46 |

TABLE 5

Urinary levels of metabolite 1, metabolite 2 and metabolite 5 (10th day) after repeated administration of three 200 mg capsules of ipriflavone per day (mean values ± S.D.)

|  |  | (0–24) | | | (24–48) | | |
|---|---|---|---|---|---|---|---|
|  |  | ml | mg | % DOSE | ml | mg | % DOSE |
| METABOLITE 1 | Mean | 1000.00 | 6.50* | 1.08 | 983.75 | 2.11* | 0.35 |
|  | S.D. | 109.02 | 0.69 | 0.11 | 80.15 | 0.37 | 0.06 |
| METABOLITE 2 | Mean | 1000.00 | 4.21* | 0.70 | 983.75 | 1.10* | 0.18 |
|  | S.D. | 109.02 | 0.77 | 0.13 | 80.15 | 0.26 | 0.04 |
| METABOLITE 5 | Mean | 1000.00 | 12.72* | 2.12 | 983.75 | 4.91* | 0.82 |
|  | S.D. | 109.02 | 2.70 | 0.45 | 80.15 | 1.18 | 0.20 |

*significant difference compared with the capsules. Mann-Whitney U test ($p<0.05$)

To confirm the preliminary results we performed a further study to directly compare the bioavailability of ipriflavone and its metabolites, given orally on multiple dosing as 2 forms: 200 mg standard tablets and 300 mg capsules.

In this comparative study all the conditions that could influence in some measure the bioavailability behaviour such as meals, drug administration or samples collection were strictly standardized.

The study was carried out in twelve young healthy volunteers in good health.

All the subjects were on a standard diet for all the period of the study.

For each treatment, after an overnight fast, each subject received at 8:00 a.m. on Day 1 the first oral dosing. From Day 1 to Day 10 the daily doses were administered during the meals. The two different treatments (A and B) were the following:

Treatment A: one 200 mg Ipriflavone Tablet 3 times daily at 8:00 a.m. , 1:00 p.m. and 8:00 p.m.;

Treatment B: one 300 mg Ipriflavone Scherer capsule two times daily at 8:00 a.m. and 8:00 p.m.

A wash-out period of two weeks or more was observed between two subsequent treatments.

Blood samples were collected on the first day before starting the treatment, and at the steady-state during day 10, following a suitable sampling schedule established in order to compare the bioavailability of the two compositions during the whole 24-hour period, taking into account the different dosage scheme.

Urine samples were collected prior to the drug administration and then on day 10, quantitatively, by fractions corresponding to time administration intervals (treatment A: 0.5/5–12/12–24 hours; treatment: B 0–12 and 12–24 hours).

The quantitative measurement of ipriflavone and its metabolites (M1, M2, M3 and M5) in biological specimens was performed by HPLC assay with UV detection before and after enzymatic hydrolysis of the biological samples.

Plasma levels of ipriflavone could not be quantified in several subjects, precluding complete pharmacokinetic study of the compound.

This confirms the extensive metabolization of the product in man.

Pharmacokinetic parameters characteristic of metabolites M1, M2, M3 and M5 (free+conjugated; mean± sem values) are presented in Tables 6 to 9 in which Cmax, Cmin, AUC have the same meaning expressed before and Ae % is the total amount excreted in urine expressed in percentage of the daily dose of ipriflavone administered, after correction for difference in molecular weight of the metabolites.

TABLE 6

Pharmacokinetic parameters characteristic of
total (free + conjugated) metabolite M1, at
steady-state following treatments A and B
(mean ± sem values).

|  | TREATMENT A (3 × 200 mg/day) | TREATMENT B (2 × 300 mg/day) | STATISTICS |
|---|---|---|---|
| $C_{max}$ (ng · ml$^{-1}$) | 377 ± 59 | 525 ± 58 | p<0.001 |
| $AUC_{0-24}$ (ng · ml$^{-1}$ · h) | 5092 ± 625 | 6651 ± 778 | p<0.01 |
| $C_{max}/C_{min}$ | 3.45 ± 0.36 | 3.73 ± 0.40 | NS |
| Ae (%) | 4.84 ± 0.51 | 3.41 ± 0.41 | p<0.05 |

TABLE 7

Pharmacokinetic parameters characteristic of
total (free + conjugated) metabolite M2, at
steady-state following treatments A and B
(mean ± sem values).

|  | TREATMENT A (3 × 200 mg/day) | TREATMENT B (2 × 300 mg/day) | STATISTICS |
|---|---|---|---|
| $C_{max}$ (ng · ml$^{-1}$) | 386 ± 66 | 431 ± 75 | NS |
| $AUC_{0-24}$ (ng · ml$^{-1}$ · h) | 5704 ± 830 | 6711 ± 1134 | p<0.01 |
| $C_{max}/C_{min}$ | 2.93 ± 0.35 | 2.47 ± 0.21 | NS |
| Ae (%) | 3.86 ± 0.58 | 3.05 ± 0.37 | p<0.05 |

TABLE 8

Pharmacokinetic parameters characteristic of
total (free + conjugated) metabolite M3, at
steady-state following treatments A and B
(mean ± sem values).

|  | TREATMENT A (3 × 200 mg/day) | TREATMENT B (2 × 300 mg/day) | STATISTICS |
|---|---|---|---|
| $C_{max}$ (ng · ml$^{-1}$) | 313 ± 44 | 648 ± 96 | p<0.01 |
| $AUC_{0-24}$ (ng · ml$^{-1}$ · h) | 4226 ± 777 | 6701 ± 1180 | p<0.01 |
| $C_{max}/C_{min}$ | 4.56 ± 0.57 | 6.59 ± 1.04 | NS |
| Ae (%) | 2.42 ± 0.27 | 3.37 ± 0.53 | p<0.05 |

TABLE 9

Pharmacokinetic parameters characteristic of
total (free + conjugated) metabolite M5, at
steady-state following treatments A and B
(mean ± sem values).

|  | TREATMENT A (3 × 200 mg/day) | TREATMENT B (2 × 300 mg/day) | STATISTICS |
|---|---|---|---|
| $C_{max}$ (ng · ml$^{-1}$) | 747 ± 125 | 1003 ± 68 | NS |
| $AUC_{0-24}$ (ng · ml$^{-1}$ · h) | 10092 ± 1403 | 12344 ± 980 | NS |
| $C_{max}/C_{min}$ | 3.39 ± 0.43 | 4.20 ± 0.37 | NS |
| Ae (%) | 12.42 ± 1.46 | 13.88 ± 1.50 | NS |

This study confirms that the oily vehiculation improves the absorption of ipriflavone.

Infact, after administration of capsules, metabolites M1, M2 and M3 show at steady-state, a significant increase in $AUC_{0-24h}$. For metabolite M5, $AUC_{0-24h}$ was not sgnificantly increased.

Ipriflavone 300 mg, administered as Scherer capsule, produces a mean increment in bioavailability equal to 35%.

In urine, no unchanged ipriflavone levels were found in each treatment. The urinay excretion of ipriflavone metabolites was similar (M2, M3, M5).

The simplified dosage scheme obtained with 300 mg capsules does not modify, at steady-state, the mean plasma levels of ipriflavone metabolites, as demonstrated the Cmax/Cmin ratios calculated on a daily basis for each formulation.

The good bioavailability of capsules allows simplifying the dosage scheme by reducing the daily administrations (twice daily instead of 3 times daily) and improving compliance. This fact is not negligible, also taking into account the considerable mean age of patients and long-term treatment.

We claim:

1. An orally administerable pharmaceutical composition in unit dosage form having antiosteoporotic and antihypercalcemic properties consisting essentially of 300–600 mg of ipriflavone as the principal active ingredient together with a vehicle selected from the group consisting of hydrogenated vegetable oils, glycerides, white chocolate, soya lecithin and mixtures thereof, said vehicle being present in an amount of at least 50% by weight of the unit dose.

2. A process for treating a subject suffering from osteoporosis or hypercalcemia which consists of orally administering to said subject a pharmaceutical composition according to claim 1.

* * * * *